United States Patent

Fowler

[11] 4,182,155
[45] Jan. 8, 1980

[54] METHOD AND APPARATUS FOR ZERO POINT CALIBRATION OF ULTRASONIC THICKNESS GAUGE

[75] Inventor: Kenneth A. Fowler, Medfield, Mass.
[73] Assignee: Panametrics, Inc., Waltham, Mass.
[21] Appl. No.: 944,741
[22] Filed: Sep. 22, 1978
[51] Int. Cl.² ............................................ G01N 29/00
[52] U.S. Cl. ..................................... 73/1 DV; 73/644
[58] Field of Search ............. 73/1 DV, 644, 609, 627

[56] References Cited
U.S. PATENT DOCUMENTS
3,918,296  11/1975  Kitada .................................. 73/627

*Primary Examiner*—Anthony V. Ciarlante
*Attorney, Agent, or Firm*—Kenway & Jenney

[57] ABSTRACT

A transducer for an ultrasonic thickness gauge of the pitch and catch type has transmitting and receiving transducer elements on adjoining blocks of delay material separated by an acoustic barrier is calibrated by operating the receiving transducer element in pulse-echo mode. The lengths of the two delay blocks differ by an amount calculated to make the pulse-echo travel time in the longer delay block greater than pitch and catch travel time by an amount at least equal to the geometric delay of the transducer to provide an unambiguous readout during pulse-echo operation when the gauge is adjusted to the proper zero point calibration for the transducer.

6 Claims, 3 Drawing Figures

METHOD AND APPARATUS FOR ZERO POINT CALIBRATION OF ULTRASONIC THICKNESS GAUGE

BACKGROUND OF THE INVENTION

The invention relates to ultrasonic thickness gauges and particularly to a transducer construction and gauge calibration method that provides for self-calibration of the zero time point of the gauge without a test block.

Ultrasonic measurements of thickness are most commonly made by timing the interval for an ultrasonic wave pulse to traverse a sheet or plate, and converting the measured time to thickness. Some ultrasonic thickness gauges such as those designed for corrosion work utilize so-called "dual element", or "pitch-and-catch", transducers. The ultrasonic wave pulse is transmitted by a "pitch" transducer, mounted on a block of material, through the material to the piece to be measured. The wave pulse is reflected from the back side of the piece and received by a "catch" transducer, similarly mounted on a block of material.

This dual transducer design is used because it provides greater thin-range resolution and signal-to-noise ratio on the rough surface produced by corrosion. The blocks of material on which the transducers are mounted provide a barrier between the transducer elements and the piece to which the transducer is applied, and add a time delay to the time interval required for the wave to traverse the material being measured. Each transducer element is mounted on a different block of delay material, and the blocks are separated by an acoustic barrier to prevent ultrasonic waves passing directly from one block to the other.

Because the blocks of delay material add a time delay in the passage of the interrogating wave pulse signal, the zero time point for the time interval measurement, from which the thickness of the piece is derived, is not coincident with the transmission of the signal, but instead occurs at some time a few microseconds later. The exact zero time point is determined by the length and sound velocity of the delay material and the geometry of the transducer assembly. A zero point calibration adjustment is provided on the instrument to electronically set the zero time point.

For ultrasonic thickness gauging instruments of this type presently available, the zero point calibration is accomplished by coupling the transducer to a test block of known thickness and adjusting the instrument until the known correct thickness of the test block is displayed. However, the zero point of the transducer can change due to variations in temperature or due to wear of the blocks of delay material. In particular, if transducer utilizing plastic delay materials are used to make measurements on hot surfaces, the zero point calibration must be frequently checked in order to compensate for the change in sound velocity in the delay material as it heats up. The frequent use of a test block to reset the zero point is undesirable. It requires time, and care, and both hands interrupting the measurement procedure, and requires the availability of the test block.

Accordingly, it is a principal object of the invention to provide an apparatus and method for the zero point calibration of an ultrasonic thickness gauge without requiring use of a test block.

Another principal object of the invention is to provide a means of self-calibration of an ultrasonic thickness gauge that automatically compensates for changes of temperature of delay material or changes in length due to wear of the delay material blocks.

Still another object of the invention is to provide a construction and method for such a self-calibration that is simple in design, reliable and accurate in use, convenient to operate and inexpensive to produce.

SUMMARY OF THE INVENTION

A transducer for a self-calibrating ultrasonic thickness gauge comprises first and second blocks of delay material and an acoustic barrier separating the blocks, a first transducer means mounted on the first block capable of transmitting ultrasonic waves, and a second transducer means mounted on the second block, capable of receiving ultrasonic waves during pitch-and-catch operation of the gauge, and also being capable of operation in the pulse-echo mode, in which the second block has a configuration such that an ultrasonic wave passing through the second block has a longer path than the path of the wave in the first block, the difference between the lengths of wave paths in the blocks being selected so that the difference in time of wave travel through the blocks due to the difference in paths offsets the geometric time delay in transmission of an ultrasonic wave through the transducer in the pitch-and-catch mode. In preferred embodiments the blocks are the same material, and the lengths of the blocks define the ultrasonic wave path, the length of the second block being greater than the length of the first block by an amount selected so that the difference in lengths offsets the geometric time delay in transmission of an ultrasonic wave during pitch-and-catch mode operation. Also, the gauge includes switching means for switching from operation in the pitch-and-catch mode to operation in a pulse-echo mode.

The invention further includes the method of calibrating such a gauge having a means for readout of the time traveled by the wave, namely, providing for the second block to have a longer wave path than the first block for passage of the wave operating the receiving transducer means in a pulse-echo mode, and calibrating the readout means to read a predetermined reference number, the longer wave path being chosen to offset the geometric time delay. In the preferred embodiment the method further includes operating the gauge in the pitch and catch mode with a test block, calibrating the readout means to the known value of the test block, removing the test block, and operating the receiving transducer means in a pulse-echo mode to obtain the reference number on the display.

DESCRIPTION OF A PREFERRED EMBODIMENT

Figure 1:
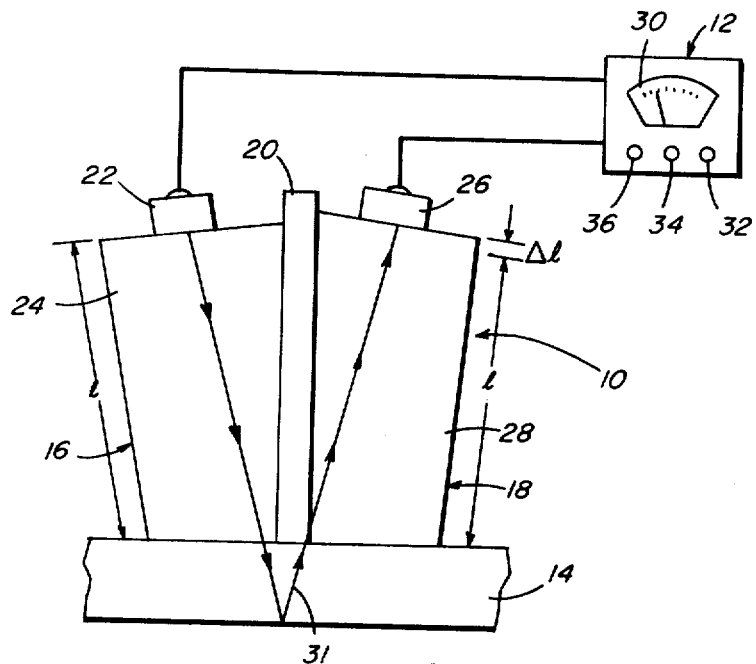
FIG. 1 is a view in cross section of a transducer constructed in accordance with the principles of the invention.

Referring to FIG. 1, an ultrasonic transducer 10 is electrically coupled to an ultrasonic thickness gauge and readout circuitry unit 12. For purposes of illustrating the transducer's normal function, it is shown in FIG.

1 coupled to a sheet of material 14, whose thickness is to be measured.

Transducer 10 is of the "pitch-and-catch" type used in thickness measurement. It has a transmitting portion 16 and a receiving portion 18. These two portions are separated by an acoustic barrier 20.

Transmitting portion 16 includes a transmitting transducer element 22 coupled to a block of delay material 24. Delay material 24 is made of some suitable composition, typically plastic. Receiving portion 18, in similar fashion, has a receiving transducer element 26 coupled to a block of similar delay material 28.

The thickness gauge readout circuitry unit 12, shown in FIG. 1, includes a display 30 for displaying a number corresponding to the time it takes for sound transmitted by transmitting transducer element 22 to pass through the transmitting delay material 24, the sheet of material 14, reflect off the back surface of the material, pass back through the material, and pass through the receiver delay material 28 to receiving transducer element 26. The path is illustrated by the series of arrows 31. The readout display 30 provides a display of the elapsed time, or it can be calibrated to read thickness, given the value of C, sound velocity, for the material tested. The appropriate circuitry for the circuitry unit 12 and connections to the transducers are of conventional design well known to those skilled in the art.

A principal feature of this invention is in construction of the transducer. More specifically, the material of block 24 and block 28 are as alike as possible (preferably, they are cut side by side from the same piece of stock) except that one block, the block 28 as shown, is longer to provide a small difference in the length of the delay material in the transmitting portion 16 and the receiving portion 18. This difference in length is known and is carefully controlled for transducers of a given type.

Finally, the connections of the circuitry unit 12 to the elements of the transducer are such that a switch 32 in the circuitry unit is provided to permit an excitation pulse to be applied to the transmitter transducer element 22. Another switch 34 provides for an excitation pulse to be applied to the receiver transducer element 26 so that, with this switch activated, the transducer 10 acts in a pulse-echo mode rather than a pitch-and-catch mode. That is, the ultrasonic sound wave is both transmitted and received by the receiver portion 18 of the transducer.

Figure 2:
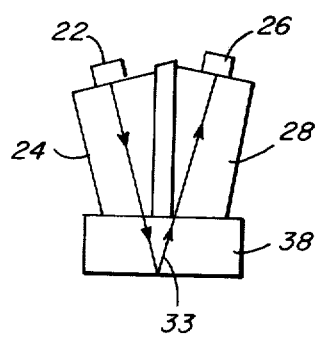
FIG. 2 is a simplified view of the transducer shown in FIG. 1, illustrating its operation in the "pitch-and-catch" mode.
Figure 3:
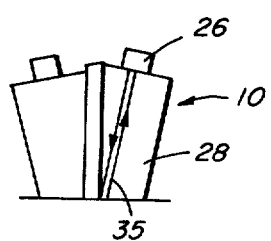
FIG. 3 is a view corresponding to FIG. 2, illustrating the transducer's operation in the "pulse-echo mode.

The other two figures of the drawing illustrate the transducer 10 used in its pitch-and-catch mode with a test block 38 of known thickness, in FIG. 2, and the subsequent use of the transducer 10 in a pulse-echo mode without a test block, in FIG. 3.

Referring to FIG. 2, transducer 10 is coupled to a test block 38 of some known thickness, for example 5 millimeters. Switch 32 provides for an electronic excitation pulse to be applied to transducer element 22. The sound pulse thereby generated travels along the path 33 and is detected by transducer element 26. Readout display 30 on unit 12 displays a number corresponding to the time it took the sound pulse to travel from transducer element 22 to transducer element 26. With a given C or sound velocity for the test block material, the display can be calibrated to read in terms of distance. Calibration dial 36 is then used to adjust the display 30 for a reading corresponding to the known thickness of test block 38. With this calibration the actual time elapsed is corrected by subtracting a time equal to the sum of the time the sound wave traveled through the transmitter delay material 24, the time sound traveled through the receiver delay material 28, and some time delay attributable to the overall geometry of the dual design of the transducer 10. After the subtraction, the remaining time is due to the passage of the sound wave through the test material only. The zero calibration having been made in this conventional manner, the test block 38 is removed.

FIG. 3 illustrates an alternate method according to this invention for self-calibrating the gauge. With the gauge calibrated by the test block, so that a zero point is set, the gauge is put in the pulse-echo mode and a reading is obtained that becomes the reference reading for future calibration of the gauge without a test block. The procedure is as follows.

By means of switch 34 an excitation pulse, greatly attenuated, is applied to transducer element 26. Transducer 10 is now operating in the pulse-echo mode rather than the normal pitch-and-catch mode. Accordingly, display 30 will now show a number that accounts for the travel of the sound pulse back and forth through the receiver delay material 28 as illustrated by the arrows 35.

It must be remembered that readout 30 has been calibrated to account for (by subtracting) a time delay created by the use of transducer 10 in the pitch-and-catch mode. That time delay was equal to a sum of times that can be illustrated by the equation:

$$T_1 = T_t + T_r + T_g,$$

where $T_t$ is the amount of time for sound to travel through transmitter material 24, $T_r$ equals the time the sound travels through receiving material 28, and $T_g$ equals the time delay due to the geometry of the transducer 10. This geometric time delay is thus seen to be the portion of the time delay not attributable to the time of passage of the ultrasonic wave through the two blocks of delay material 24 and 28.

The time traveled by the sound wave during the use of the transducer 10 in the pulse echo mode is shown by the following equation:

$$T_2 = 2T_r,$$

where $T_r$ is the amount of time it takes sound to travel through the receiver delay material 28, since what essentially happens is that the pulse-echo mode, the sound wave travels back and forth in the receiver portion of the transducer.

Since the number, N, on the display 30 has been adjusted when the test block 38 was used in the pitch-and-catch mode, it shows a subtraction of $T_1$ from the real time traveled by a sound pulse. Accordingly, when the pulse-echo mode is used, the number, N', appearing on the display 30 corresponds to the difference between $T_2$ and $T_1$, as shown by the following equation:

$$N' = K(T_2 - T_1),$$

where K is the constant that was used to convert time to a thickness measurement for the test block.

Since the receiver delay 28 is slightly longer than the transmitting delay 24, by $\Delta l$, the difference between $T_r$ and $T_t$, or $\Delta T$, is a function of $\Delta l$ (by virtue of keeping the material in both delay materials as alike as possible), as illustrated by the equation:

$\Delta T = \Delta l / V_1,$ where V is the wave velocity in the delay material.

Substituting $T_t + \Delta T$ for $T_r$ in the equations, we obtain a value for N', shown by:

$$N' = K(T_2 - T_1)$$
$$= K[(2T_r) - (T_t + T_r + T_g)]$$
$$= K(\Delta T - T_g).$$

To offer a particular example, a transducer has a difference in length, $\Delta l$, between receiver and transmitter delay elements, of 0.062 inch, and $V_1$, sound velocity in the plastic delay material used, is 0.101 in/μs at room temperature. The constant K is equal to 0.234/2 in/μs with the gauge calibrated for steel.

In a particular transducer used, a time delay due to geometry, typical of such transducers, is 0.239 μs. The number, N', to be used as a future reference for self-calibrating the gauge without a test block, then, is:

$$N' = K(\Delta T - T_g)$$

$$N' = K(\Delta T - T_g)$$

$$N' = \frac{0.234}{2} \left( \frac{0.062}{0.101} - 0.239 \right)$$

$$= 0.117(0.613 - 0.24)$$

$$= 0.044$$

It is important to note that the introduction of a change in length of the delay material between the transmitting and receiving portions of the transducer is essential to this calibration method. Without it, the formulas above reduce to N' being a negative value, solely a function of $T_g$, or dependent only on the geometric time delay. This means that the zero time point is greater than the pulse-echo travel time in a receiver delay element that is equal in length to the transmitting delay element and of the same material. This condition makes it impossible to calibrate the gauge electronically without the use of a test block.

The difference in length of the delay elements is then selected such that the difference in pulse-echo travel time is at least equal to the geometric delay time.

With the gauge calibrated once to find the reference number, N', of the transducer, it can be calibrated again just by placing it in the pulse-echo mode and setting the readout display 30 for N'.

The calibration will be reasonably valid when changes in temperature affect the velocity of sound in the delay material ($V_1$). For example, using the rule of thumb for plastics that the temperature coefficient of sound velocity is 0.1% per degree Centigrade, a uniform temperature increase of 50 degrees Centigrade would result in a 5% change in transit time. For the same transducer design that has a time delay of 9 μs at room temperature, the delay would increase to 9 μs at 50 degrees above room temperature. This would result in an error in the thickness reading of steel of 0.052" unless corrected.

Assuming that the pulse-echo mode calibration had been used to calibrate the gauge at this high temperature, the error that would be introduced into any reading is computed as follows:

$$N' = K(\Delta T - T_g)$$

At room temperature $$N' = \frac{0.234}{2} \left( \frac{0.062}{0.101} - 0.239 \right)$$

$$= 0.117(0.613 - 0.239)$$

At 50 degrees Centigrade above room temperature, the sound velocity decreases 5%, from 0.101 in/μs to 0.096 in/μs. Then, $$N'' = \frac{0.234}{2} \left( \frac{0.062}{0.096} - 0.239 \right)$$

$$= 0.117(0.646 - 0.239)$$

$$= 0.048$$

The error introduced is the difference between the two, or 0.004", or about 8% of the error that would have been introduced if this opportunity for pulse-echo mode calibration had not been available.

Furthermore, since N' is dependent on the difference in length of the delay elements and not the length itself, N' is substantially independent of wear of the elements, provided that, as usually occurs, the elements wear uniformly.

Preferably, the initial calibration of a transducer with a test block is done where the transducer is assembled, and the reference number N' is engraved on the transducer. No further calibration by means of a test block is ordinarily necessary. The reference number can be checked with a test block, however, whenever that is thought necessary.

Only a particular embodiment of the method and apparatus of the invention having been described, the scope of the invention will allow others skilled in the art to produce other embodiments within the scope of the invention, as set out in the following claims.

I claim:

1. A transducer comprising
   a first block of delay material,
   a second block of delay material,
   an acoustic barrier separating said blocks,
   a first transducer means mounted on said first block, capable of transmitting ultrasonic waves, and
   a second transducer means mounted on said second block, capable of receiving ultrasonic waves during pitch-and-catch operation of said transducer, said second transducer means further being capable of operation in the pulse-echo mode,
   in which said second block has a configuration such that an ultrasonic wave passing through said second block during operation of said transducer has a longer path than the path of said wave through said first block,
   the difference between the lengths of wave paths in said blocks being selected so that the difference in time of wave travel through said blocks due to said difference in paths is at least as great as the geometric time delay in transmission of an ultrasonic wave through said transducer in the pitch-and-catch mode.

2. The transducer as claimed in claim 1 in which said blocks are of the same material.

3. The transducer as claimed in claim 2 in which each said block has a length defining the dimension of the path of the ultrasonic wave passing through the block during operation of the gauge, the length of said second block being greater than the length of said first block by an amount selected so that the difference in time of wave travel through said blocks due to said difference in lengths is at least as great as the geometric time delay in transmission of an ultrasonic wave through said transducer in the pitch-and-catch mode.

4. The transducer as claimed in claim 1 further including switch means for switching said transducer from operation in the pitch-and-catch mode, using said first and second transducer means, to operation in the pulse-echo mode, using said second transducer means.

5. A method for self-calibration of an ultrasonic gauge of the pitch-and-catch type, having an ultrasonic wave transmitting transducer means mounted on a first block of delay material, an ultrasonic wave receiving transducer means mounted on a second block of delay material, and a means for readout of the time travelled by said wave, and an acoustic barrier between said blocks, comprising the steps of:

providing for said second block to have a longer wave path than said first block for passage of said ultrasonic wave, operating said receiving transducer means in a pulse echo mode, and calibrating said readout means to read a predetermined reference number, said longer wave path being chosen to produce a wave transmission delay at least as great as the geometric time delay transmission of an ultrasonic wave through said transducer in the pitch-and-catch mode.

6. The method of claim 5 further including operating said gauge in the pitch-and-catch mode with a test block, calibrating said readout means to the known value of said test block, removing said test block, and operating said receiving transducer means in a pulse-echo mode to obtain said reference number.

* * * * *